(12) United States Patent
Cazzato et al.

(10) Patent No.: US 7,150,731 B2
(45) Date of Patent: Dec. 19, 2006

(54) DISPOSABLE ABSORBENT UNDERPANTS

(75) Inventors: Tim Richard Cazzato, Bloomingdale, IL (US); Paul Joseph Datta, Appleton, WI (US); Jacqueline Ann Gross, Neenah, WI (US); Michael Barth Venturino, Appleton, WI (US); Steven Lambert Weyenberg, Kaukauna, WI (US); Michael Scott Brunner, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 337 days.

(21) Appl. No.: 10/932,779

(22) Filed: Sep. 2, 2004

(65) Prior Publication Data

US 2005/0055001 A1 Mar. 10, 2005

Related U.S. Application Data

(63) Continuation-in-part of application No. 09/566,465, filed on May 8, 2000, now abandoned, which is a continuation-in-part of application No. 08/971,389, filed on Nov. 11, 1997.

(51) Int. Cl.
*A61F 13/15* (2006.01)
*A61F 13/20* (2006.01)

(52) U.S. Cl. ............... 604/385.27; 604/385.25; 604/385.01; 604/385.24

(58) Field of Classification Search .......... 604/385.01, 604/385.101, 385.24–385.3, 386–387, 396
See application file for complete search history.

(56) References Cited

U.S. PATENT DOCUMENTS

| | | | |
|---|---|---|---|
| 2,119,610 A | 6/1938 | Tasker | |
| 2,125,495 A | 8/1938 | French | |
| 2,408,723 A | 10/1946 | Arpin et al. | |
| 2,733,715 A | 2/1956 | Folk | |
| 2,866,459 A | 12/1958 | Sobelson | |
| 3,371,668 A | 3/1968 | Johnson | |
| 3,468,748 A | 9/1969 | Bassett | |
| 3,488,778 A | 1/1970 | Goujon | |
| 3,575,782 A | 4/1971 | Hansen | |
| 3,599,640 A | 8/1971 | Larson | |
| 3,912,565 A | 10/1975 | Koch et al. | |

(Continued)

FOREIGN PATENT DOCUMENTS

CA 2 040 578 10/1991

(Continued)

OTHER PUBLICATIONS

American Society for Testing Materials (ASTM) Designation: D2495-87, "Standard Test Method for Moisture in Cotton by Oven-Drying," pp. 617-622, published Sep. 1987.

(Continued)

*Primary Examiner*—Michele Kidwell
(74) *Attorney, Agent, or Firm*—Thomas J. Connelly

(57) ABSTRACT

A disposable absorbent article is disclosed having a waist opening and a pair of leg openings. The absorbent article has first, second and third pairs of leg elastics secured between an outer cover and an inner liner. The first, second and third leg elastics are arranged around each of the pair of leg openings with each of the third pair of leg elastics being positioned intermediate one of each of the first and second pairs of leg elastics. Each of the third pair of leg elastics is also separated from one of the first pair of leg elastics by a first gap and from one of the second pair of leg elastics by a second gap.

20 Claims, 4 Drawing Sheets

U.S. PATENT DOCUMENTS

| | | |
|---|---|---|
| 3,985,003 A | 10/1976 | Reed |
| 4,022,212 A | 5/1977 | Lovison |
| 4,081,301 A | 3/1978 | Buell |
| 4,093,204 A | 6/1978 | Landgraf et al. |
| 4,196,245 A | 4/1980 | Kitson et al. |
| 4,205,679 A | 6/1980 | Repke et al. |
| 4,210,143 A | 7/1980 | De Jonckheere |
| 4,227,531 A | 10/1980 | Mcleod |
| 4,227,952 A | 10/1980 | Sabee |
| 4,236,257 A | 12/1980 | Williams et al. |
| 4,240,866 A | 12/1980 | Rega |
| 4,241,462 A | 12/1980 | Tagawa et al. |
| 4,244,059 A | 1/1981 | Pflaumer |
| 4,244,367 A | 1/1981 | Rollenhagen |
| 4,253,461 A | 3/1981 | Strickland et al. |
| 4,269,188 A | 5/1981 | Nishizawa et al. |
| 4,285,342 A | 8/1981 | Mesek |
| 4,297,157 A | 10/1981 | Van Vliet |
| 4,300,241 A | 11/1981 | Shaull |
| 4,300,562 A | 11/1981 | Pieniak |
| 4,300,967 A | 11/1981 | Sigl |
| 4,302,853 A | 12/1981 | Mesek |
| 4,304,021 A | 12/1981 | Theodorsen |
| 4,323,070 A | 4/1982 | Ternstrom et al. |
| 4,325,372 A | 4/1982 | Teed |
| 4,327,448 A | 5/1982 | Lunt |
| 4,338,939 A | 7/1982 | Daville |
| 4,344,999 A | 8/1982 | Gohlke |
| 4,351,340 A | 9/1982 | Mcleod |
| D266,591 S | 10/1982 | Ryan |
| 4,352,355 A | 10/1982 | Mesek et al. |
| 4,352,356 A | 10/1982 | Tong |
| 4,355,425 A | 10/1982 | Jones et al. |
| 4,385,224 A | 5/1983 | Kaufman et al. |
| 4,390,999 A | 7/1983 | Lawson et al. |
| 4,397,645 A | 8/1983 | Buell |
| 4,405,536 A | 9/1983 | Woodcock |
| 4,407,284 A | 10/1983 | Pieniak |
| 4,409,049 A | 10/1983 | Passafiume et al. |
| 4,411,660 A | 10/1983 | Dawn et al. |
| 4,412,881 A | 11/1983 | Sigl |
| 4,425,127 A | 1/1984 | Suzuki et al. |
| 4,425,128 A | 1/1984 | Motomura |
| 4,427,408 A | 1/1984 | Karami et al. |
| 4,430,086 A | 2/1984 | Repke |
| 4,432,823 A | 2/1984 | Moore |
| 4,450,026 A | 5/1984 | Pieniak et al. |
| 4,490,148 A | 12/1984 | Beckestrom |
| 4,498,944 A | 2/1985 | Krause et al. |
| 4,499,139 A | 2/1985 | Schortmann |
| 4,501,792 A | 2/1985 | Holmes et al. |
| RE31,922 E | 6/1985 | Mesek et al. |
| 4,522,874 A | 6/1985 | Pommez |
| 4,534,769 A | 8/1985 | De Jonckheere et al. |
| 4,536,181 A | 8/1985 | Cook |
| 4,548,859 A | 10/1985 | Kline et al. |
| 4,552,795 A | 11/1985 | Hansen et al. |
| 4,555,244 A | 11/1985 | Buell |
| 4,555,245 A | 11/1985 | Armbruster |
| 4,555,811 A | 12/1985 | Shimalla |
| 4,560,381 A | 12/1985 | Southwell |
| 4,573,986 A | 3/1986 | Minetola et al. |
| 4,585,448 A | 4/1986 | Enloe |
| 4,586,199 A | 5/1986 | Birring |
| 4,597,110 A | 7/1986 | Smith, Sr. et al. |
| 4,601,717 A | 7/1986 | Blevins |
| 4,606,079 A | 8/1986 | Dewoskin |
| 4,610,680 A | 9/1986 | Lafleur |
| 4,610,681 A | 9/1986 | Strohbeen et al. |
| 4,612,674 A | 9/1986 | Hashimoto |
| 4,615,051 A | 10/1986 | Hashimoto |
| 4,615,695 A | 10/1986 | Cooper |
| 4,619,649 A | 10/1986 | Roberts |
| 4,626,305 A | 12/1986 | Suzuki et al. |
| 4,629,643 A | 12/1986 | Curro et al. |
| 4,636,207 A | 1/1987 | Buell |
| 4,639,949 A | 2/1987 | Ales et al. |
| 4,640,859 A | 2/1987 | Hansen et al. |
| 4,641,381 A | 2/1987 | Heran et al. |
| 4,642,818 A | 2/1987 | Dehnert et al. |
| 4,642,819 A | 2/1987 | Ales et al. |
| 4,646,362 A | 3/1987 | Heran et al. |
| 4,655,760 A | 4/1987 | Morman et al. |
| 4,661,102 A | 4/1987 | Shikata et al. |
| 4,664,663 A | 5/1987 | Brier |
| 4,666,542 A | 5/1987 | De Jonckheere |
| 4,671,793 A | 6/1987 | Hults et al. |
| 4,674,135 A | 6/1987 | Greene |
| 4,675,016 A | 6/1987 | Meuli et al. |
| 4,681,580 A | 7/1987 | Reising et al. |
| 4,683,877 A | 8/1987 | Ersfeld et al. |
| 4,687,477 A | 8/1987 | Suzuki et al. |
| 4,695,278 A | 9/1987 | Lawson |
| 4,695,279 A | 9/1987 | Steer |
| 4,698,855 A | 10/1987 | Hicks |
| 4,699,823 A | 10/1987 | Kellenberger et al. |
| 4,718,902 A | 1/1988 | Bonito |
| 4,726,807 A | 2/1988 | Young et al. |
| 4,729,131 A | 3/1988 | Thygesen |
| 4,735,622 A | 4/1988 | Acuff et al. |
| 4,736,468 A | 4/1988 | Efird et al. |
| 4,743,239 A | 5/1988 | Cole |
| 4,743,241 A | 5/1988 | Igaue et al. |
| 4,745,636 A | 5/1988 | Lunt |
| 4,756,942 A | 7/1988 | Aichele |
| 4,762,582 A | 8/1988 | De Jonckheere |
| 4,771,483 A | 9/1988 | Hooreman et al. |
| 4,795,451 A | 1/1989 | Buckley |
| 4,798,603 A | 1/1989 | Meyer et al. |
| 4,813,950 A | 3/1989 | Branch |
| 4,816,026 A | 3/1989 | Richardson |
| 4,838,886 A | 6/1989 | Kent |
| 4,842,666 A | 6/1989 | Werenicz |
| 4,880,420 A | 11/1989 | Pomparelli |
| 4,880,424 A | 11/1989 | Rautenberg |
| 4,883,480 A | 11/1989 | Huffman et al. |
| 4,883,481 A | 11/1989 | Blanchard |
| 4,898,594 A | 2/1990 | Cottenden |
| 4,909,804 A | 3/1990 | Douglas, Sr. |
| 4,928,323 A | 5/1990 | Nathan |
| 4,932,949 A | 6/1990 | Thygesen et al. |
| 4,932,950 A | 6/1990 | Johnson |
| 4,938,753 A | 7/1990 | Van Gompel et al. |
| 4,938,754 A | 7/1990 | Mesek |
| 4,940,463 A | 7/1990 | Leathers et al. |
| 4,940,464 A | 7/1990 | Van Gompel et al. |
| 4,950,264 A | 8/1990 | Osborn, III |
| 4,960,414 A | 10/1990 | Meyer |
| 4,977,011 A | 12/1990 | Smith |
| 4,984,584 A | 1/1991 | Hansen et al. |
| 4,992,125 A | 2/1991 | Suzuki et al. |
| 4,995,928 A | 2/1991 | Sabee |
| 5,019,067 A | 5/1991 | Simmons |
| 5,024,667 A | 6/1991 | Malcolm et al. |
| 5,031,248 A | 7/1991 | Kemper |
| 5,037,417 A | 8/1991 | Ternstrom et al. |
| 5,055,103 A | 10/1991 | Nomura et al. |
| 5,057,571 A | 10/1991 | Malcolm et al. |
| 5,062,839 A | 11/1991 | Anderson |
| 5,069,678 A | 12/1991 | Yamamoto et al. |
| 5,074,854 A | 12/1991 | Davis |
| 5,080,741 A | 1/1992 | Nomura et al. |
| 5,087,253 A | 2/1992 | Cooper |
| 5,092,861 A | 3/1992 | Nomura et al. |

| | | | | | | |
|---|---|---|---|---|---|---|
| 5,098,422 A | 3/1992 | Davis et al. | | 5,660,666 A | 8/1997 | Dilnik et al. |
| 5,147,343 A | 9/1992 | Kellenberger | | 5,745,922 A | 5/1998 | Rajala et al. |
| 5,147,487 A | 9/1992 | Nomura et al. | | 5,746,731 A | 5/1998 | Hisada |
| 5,149,741 A | 9/1992 | Alper et al. | | 5,749,865 A | 5/1998 | Yamamoto et al. |
| D330,590 S | 10/1992 | Pressley et al. | | 6,364,863 B1 | 4/2002 | Yamamoto et al. |
| 5,158,819 A | 10/1992 | Goodman, Jr. et al. | | 6,478,786 B1 | 11/2002 | Glaug et al. |
| 5,163,932 A | 11/1992 | Nomura et al. | | 6,482,278 B1 | 11/2002 | McCabe et al. |
| D331,627 S | 12/1992 | Igaue et al. | | 6,569,139 B1 | 5/2003 | Datta et al. |
| 5,171,239 A | 12/1992 | Igaue et al. | | 2005/0055005 A1 | 3/2005 | Cazzato et al. |
| 5,171,388 A | 12/1992 | Hoffman et al. | | | | |
| 5,188,627 A | 2/1993 | Igaue et al. | | | | |
| 5,192,606 A | 3/1993 | Proxmire et al. | | | | |
| 5,197,960 A | 3/1993 | Nomura et al. | | | | |
| 5,204,997 A | 4/1993 | Suzuki et al. | | | | |
| 5,209,801 A | 5/1993 | Smith | | | | |
| 5,234,423 A | 8/1993 | Alemany et al. | | | | |
| 5,236,430 A | 8/1993 | Bridges | | | | |
| 5,241,710 A | 9/1993 | Lockhart | | | | |
| 5,246,433 A | 9/1993 | Hasse et al. | | | | |
| 5,275,589 A | 1/1994 | Bozich | | | | |
| 5,275,676 A | 1/1994 | Rooyakkers et al. | | | | |
| 5,285,531 A | 2/1994 | Nalbandian | | | | |
| 5,325,543 A | 7/1994 | Allen | | | | |
| 5,342,341 A | 8/1994 | Igaue et al. | | | | |
| 5,363,511 A | 11/1994 | Brewer | | | | |
| 5,368,584 A | 11/1994 | Clear et al. | | | | |
| 5,370,634 A | 12/1994 | Ando et al. | | | | |
| 5,389,173 A | 2/1995 | Merkatoris et al. | | | | |
| 5,413,654 A | 5/1995 | Igaue et al. | | | | |
| 5,415,649 A | 5/1995 | Watanabe et al. | | | | |
| 5,440,764 A | 8/1995 | Matsushita | | | | |
| 5,449,353 A | 9/1995 | Watanabe et al. | | | | |
| 5,486,166 A | 1/1996 | Bishop et al. | | | | |
| 5,490,846 A | 2/1996 | Ellis et al. | | | | |
| 5,496,429 A | 3/1996 | Hasse et al. | | | | |
| 5,501,756 A | 3/1996 | Rollins et al. | | | | |
| 5,507,895 A | 4/1996 | Suekane | | | | |
| 5,507,909 A | 4/1996 | Rollins et al. | | | | |
| 5,509,915 A | 4/1996 | Hanson et al. | | | | |
| 5,540,672 A | 7/1996 | Roessler et al. | | | | |
| 5,575,782 A | 11/1996 | Hasse et al. | | | | |
| 5,601,544 A | 2/1997 | Glaug et al. | | | | |
| 5,622,581 A | 4/1997 | Ducker et al. | | | | |
| 5,626,574 A | 5/1997 | Sasaki et al. | | | | |
| 5,626,711 A | 5/1997 | Herrmann | | | | |
| 5,634,917 A | 6/1997 | Fujioka et al. | | | | |
| 5,660,664 A | 8/1997 | Herrmann | | | | |
| 5,660,665 A | 8/1997 | Jalonen | | | | |

FOREIGN PATENT DOCUMENTS

| | | |
|---|---|---|
| CA | 2 121 512 | 6/1995 |
| EP | 0 048 011 A1 | 3/1982 |
| EP | 0 456 885 A1 | 11/1991 |
| EP | 0 539 703 A1 | 5/1993 |
| EP | 0 547 497 A2 | 6/1993 |
| EP | 0 412 579 B1 | 6/1994 |
| EP | 0 487 921 B1 | 9/1995 |
| EP | 0 689 815 A1 | 1/1996 |
| EP | 0 743 052 A2 | 11/1996 |
| EP | 0 753 292 A2 | 1/1997 |
| EP | 0 832 629 A2 | 4/1998 |
| EP | 0 623 331 B1 | 3/1999 |
| EP | 0 627 210 B1 | 3/2000 |
| EP | 1 027 874 A2 | 8/2000 |
| EP | 1 208 825 A2 | 5/2002 |
| GB | 2 176 692 A | 1/1987 |
| GB | 2 245 149 A | 1/1992 |
| GB | 2 253 131 A | 9/1992 |
| GB | 2 257 652 A | 1/1993 |
| JP | 58-011507 A | 1/1983 |
| JP | 03-139349 A | 6/1991 |
| JP | 04-161152 A | 6/1992 |
| JP | 04-364845 A | 12/1992 |
| WO | WO 93/17648 A1 | 9/1993 |
| WO | WO 95/06451 A1 | 3/1995 |
| WO | WO 96/23468 A1 | 8/1996 |
| WO | WO 96/40035 A1 | 12/1996 |
| WO | WO 99/25296 A1 | 5/1999 |
| WO | WO 00/02511 A1 | 1/2000 |
| WO | WO 01/85082 A1 | 11/2001 |
| WO | WO 01/97737 A1 | 12/2001 |
| WO | WO 03/015679 A1 | 2/2003 |

OTHER PUBLICATIONS

American Society for Testing Materials (ASTM) Designation: E 96-92, "Standard Test Methods for Water Vapor Transmission of Materials," pp. 702-709, published Mar. 1992.

DISPOSABLE ABSORBENT UNDERPANTS

CROSS-REFERENCE TO RELATED APPLICATION

This application is a continuation-in-part application claiming priority under 35 U.S.C. § 120 of application Ser. No. 09/566,465 entitled DISPOSABLE ABSORBENT UNDERPANTS FOR CONTAINING BODY FLUID and filed in the U.S. Patent and Trademark Office on May 8. 2000, now abandoned which is a continuation-in-part of 08/971,389 entitled DISPOSABLE UNDERPANTS and filed in the U.S. Patent and Trademark Office on Nov. 11. 1997. The entirety of both application serial number 09/566,465 and 08/971,389 are hereby incorporated by reference.

FIELD OF THE INVENTION

This invention relates to disposable absorbent underpants having a waist opening and a pair of leg openings. More specifically, this invention relates to disposable absorbent underpants having first, second and third leg elastics surrounding each leg opening and the three leg elastics are separated by first and second gaps.

BACKGROUND OF THE INVENTION

Disposable absorbent underpants have been commercially available for some time for use by infants and toddlers as diapers and training pants. Disposable absorbent underpants have also been available for use by adults suffering from incontinence. A number of such underpants have used elastics around the leg openings to form gathers so as to minimize leakage of body fluid from the underpants. When the elastic completely encircles each of the leg openings, it has been found that pressure marks can be left on the thighs of the wearer should the elastic be too tight. It has also been found that when three or more discrete sections of elastics are secured around each leg opening, that at the points where the elastics overlap one another, leakage can occur. The overlap of two sections of elastics can also create a bump or hump that can cause irritation and discomfort to the wearer of the underpants.

Now, disposable absorbent underpants have been developed which utilize three discrete elastic sections that are spaced apart from one another and are positioned about each leg opening. Each discrete elastic section is separated from an adjacent section by a gap. When three sections of leg elastics are utilized, first and second gaps will be present which separate the three elastic sections. The gaps formed between the adjacent sections prevent the elastics from overlapping one another even when the elastics contract and gather the material to which they are secured. By eliminating overlaps of the elastics around each leg opening, one can minimize and sometimes prevent the leakage of body fluid from the disposable absorbent underpants.

SUMMARY OF THE INVENTION

Briefly, this invention relates to disposable absorbent underpants for containing body fluid. The disposable underpants include an outer cover having a front portion and a back portion joined together by a crotch portion. The crotch portion has a minimum width $W_3$. An inner liner including a front portion and a back portion is attached to the outer cover. There is no inner liner situated over the crotch portion. The front and back portions of both the outer cover and the inner liner are joined together to form a waist opening and a pair of leg openings. An absorbent pad is secured to the crotch portion of the outer cover by an adhesive. The absorbent pad includes a liquid permeable cover, a liquid-impermeable baffle and an absorbent layer positioned therebetween. The absorbent pad has a width $W_2$ which is less than the width $W_3$. A first pair of leg elastics is secured between the outer cover and the inner liner at the front portion such that each of the first pair of leg elastics is positioned within 1 inch of one of the pair of leg openings. A second pair of leg elastics is secured between the outer cover and the inner liner at the back portion such that each of the second pair of leg elastics is positioned within 1 inch of one of the pair of leg openings. A third pair of leg elastics is secured between the liquid permeable cover and the liquid-impermeable baffle such that each of the third pair of leg elastics is positioned within 1 inch of one of the leg openings, intermediate one of the first and second pairs of leg elastics. Each of the third pair of leg elastics is separated from one of the first pair of leg elastics by a first gap and from one of the second pair of leg elastics by a second gap. Each of the first and second gaps is at least about 0.125 inches in dimension. The first, second and third pairs of leg elastics allow gathers to form about each of the leg openings to minimize leakage of body fluid from the disposable absorbent underpants. The disposable absorbent underpants also contain waist elastics attached between the outer cover and the inner liner at the front and back portions. The waist elastics allow gathers to form about the waist opening to minimize leakage of body fluid from the disposable absorbent underpants.

DETAILED DESCRIPTION

Figure 1:
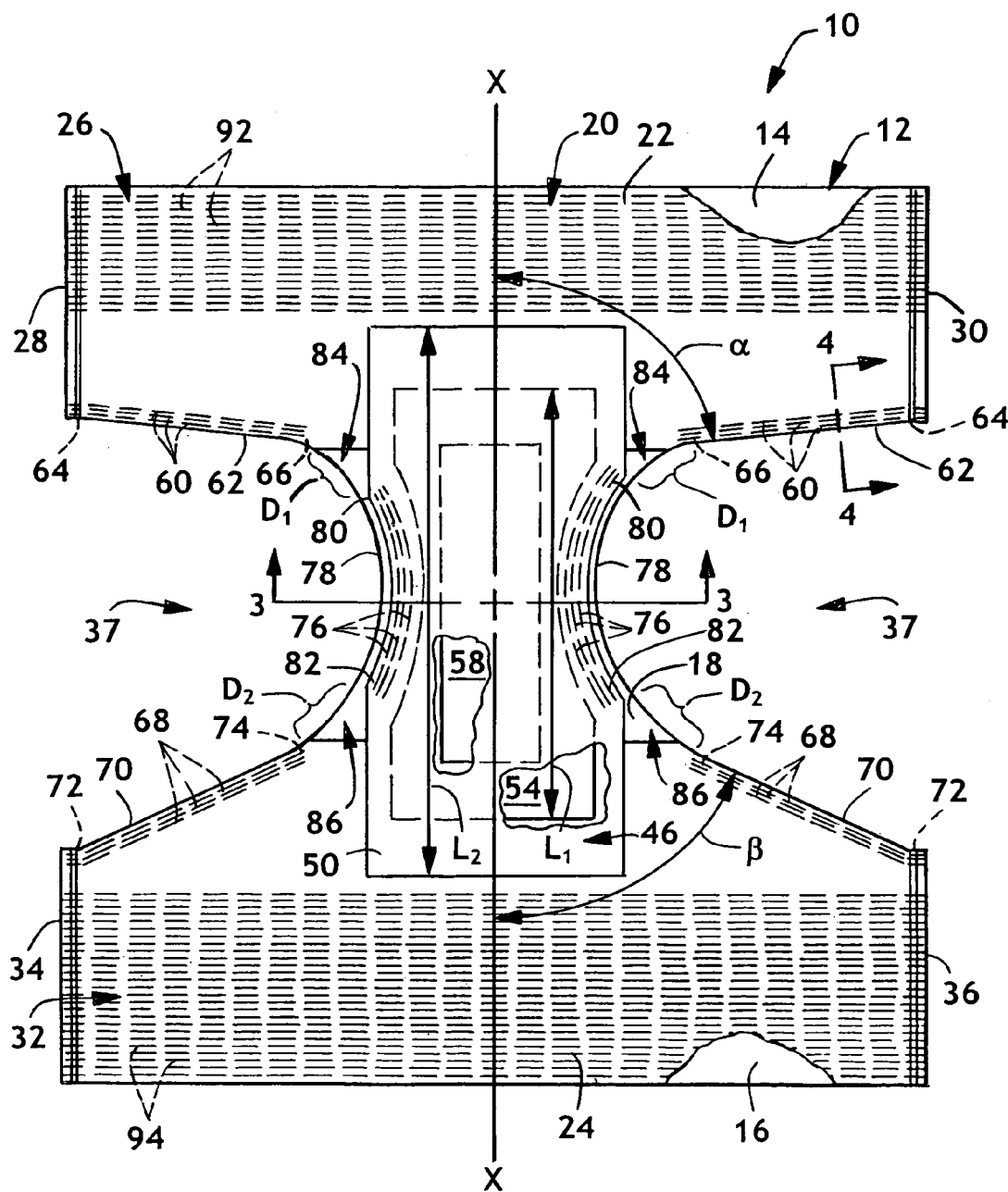
FIG. 1 is a top view of a disposable absorbent underpants before the front and back portions are joined together and showing cut-away sections depicting an outer cover, an inner liner and various layers of the absorbent pad, along with three discrete sections of leg elastics surrounding each of the pair of leg cutouts wherein each of the three-elastic sections are separated from one another by a gap.
Figure 2:
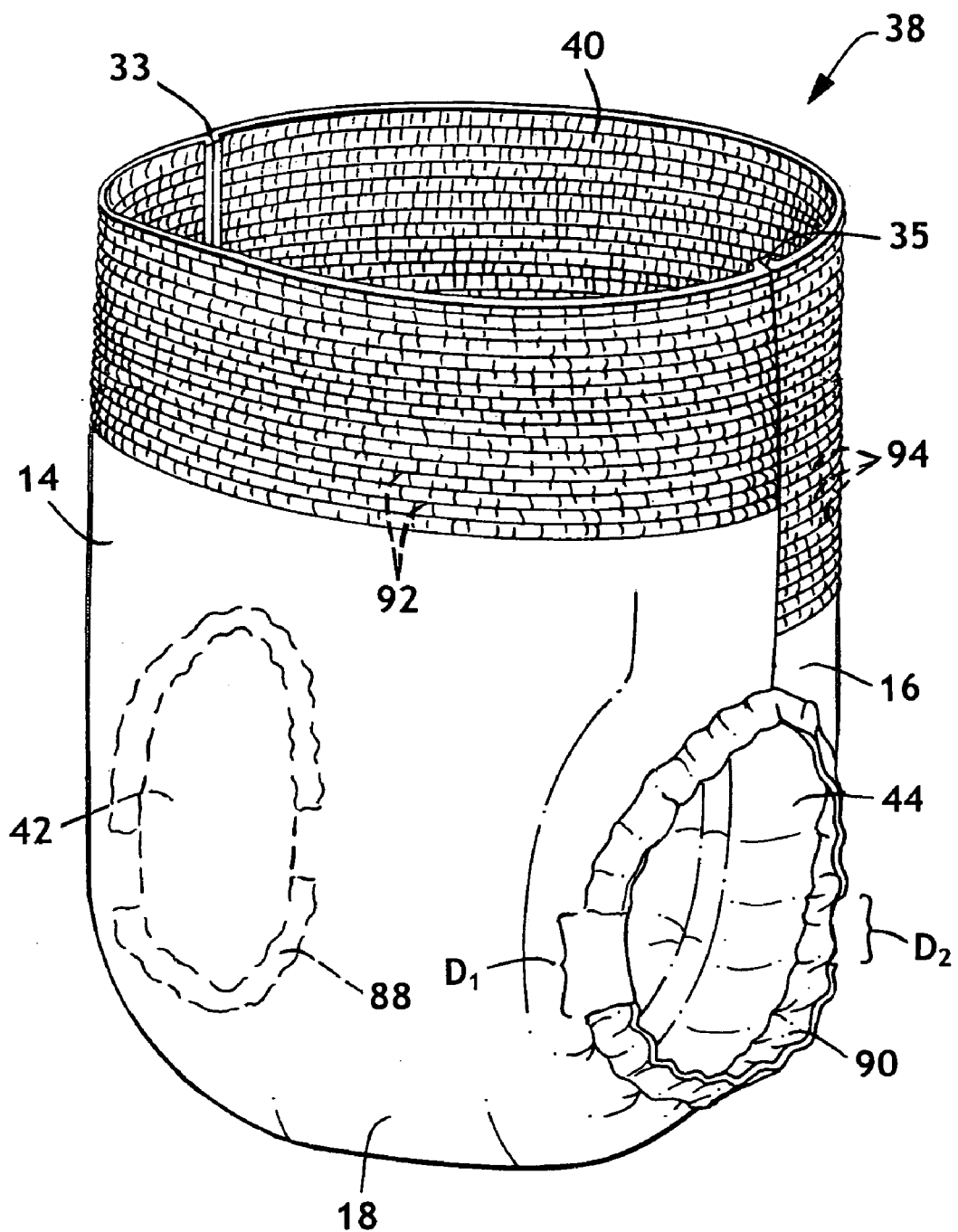
FIG. 2 is a perspective view of the disposable absorbent underpants shown in FIG. 1 when the front and back portions are joined together to form a waist opening and a pair of leg openings.

Referring to FIG. 1, a disposable absorbent underpants 10 is shown in a flat configuration before being formed into a tubular product. The tubular product is depicted in FIG. 2. The disposable absorbent underpants 10 is capable of absorbing and containing body fluid, especially urine and fecal matter. The disposable absorbent underpants 10 has a longitudinal centerline X—X when in the flat configuration. The disposable absorbent underpants 10 is manufactured and sold as a complete garment and is designed to be pulled up about the user's torso. The disposable absorbent underpants 10 can be dimensioned to be a diaper designed to be worn by an infant, a training pant designed to be worn by a toddler or an adult incontinent article that can be used day or night to absorb and contain urine and/or fecal matter.

The disposable absorbent underpants 10 is constructed of an outer cover 12 having a front portion 14 and a back portion 16 joined together by a crotch portion 18. The crotch portion 18 has an hourglass configuration. The outer cover 12 is located away from the body of the wearer in use. The outer cover 12 can be a single piece of material, as shown, or it can be made up of two or more separate pieces of material that are joined together, for example, a laminate. The outer cover 12 should be formed from a soft and flexible material. The outer cover 12 can be either liquid permeable or liquid-impermeable. Desirably, the outer cover 12 is liquid-impermeable. The outer cover 12 can be made from natural or synthetic fibers and/or films. Examples of natural fibers include cellulose wood fibers and cotton fibers. Examples of synthetic fibers include rayon fibers, polyester fibers, and polypropylene fibers. When a film is utilized, a thermoplastic film formed from a polyolefin, such as polypropylene or polyethylene works well. A combination of natural and synthetic materials can also be used to construct the outer cover 12. The outer cover 12 can also be formed from a woven or a non-woven web or sheet such as a spunbond, a meltblown or a bonded-carded web.

The disposable absorbent underpants 10 also contain an inner liner 20. The inner liner 20 is located toward the body of the wearer in use. The inner liner 20 has a front portion 22 and a back portion 24. The inner liner 20 does not have a crotch portion and the front and back portions, 22 and 24 respectively, do not extend over the crotch portion. The inner liner 20 can be two single pieces of material, as shown, or it can be made up of two or more separate pieces of material that are joined together, for example, a laminate. The inner liner 20 should be formed from a soft and flexible material. The inner liner 20 should be liquid permeable.

The inner liner 20 can be joined to, attached to or secured to the outer cover 12 by an adhesive, by sewing, by a pressure bond, by a thermal bond, by a pressure and thermal bond, or by another means known to those skilled in the art. The joining can be over the entire surface of the inner liner 20 or be over only a portion of its surface. The front portion 22 of the inner liner 20 is positioned above or over the front portion 14 of the outer cover 12 while the back portion 24 of the inner liner 20 is positioned above or over the back portion 16 of the outer cover 12. The combination of the two front portions 14 and 22 create a front waist portion 26 having distally spaced edges 28 and 30 and a pair of edges 62 each located adjacent to a leg cutout 37. The combination of the two back portions 16 and 24 create a back waist portion 32 having distally spaced edges 34 and 36 and a pair of edges 70 each located adjacent to one of the leg cutouts 37. The edges 28 and 30 of the front waist portion 26 are connected or sealed to the edges, 34 and 36 respectively, of the back waist portion 32 to form a tubular configuration 38, see FIG. 2, adaptable to fit around a person's torso.

The crotch portion 18 is formed only from the outer cover 12 and has a pair of side edges 78 each located adjacent to one of the leg cutouts 37. The side edges 78 are formed on the opposite sides of the crotch portion 18 and are arcuate in configuration. The arcuate shape of the side edges 78 give the crotch portion 18 its hourglass configuration. The hourglass configuration is more comfortable to the wearer than straight sided edges which create a rectangular shaped crotch portion. Desirably, each of the arcuate side edges 78 is a mirror image of the other side edge 78. The arcuate or curve profile of the side edges 78 allows the side edges 78 to snuggly fix against the inner thighs of the user and minimize fluid leakage. It has been found that straight sided edges formed in the crotch portion do not function as well as arcuate side edges.

Referring again to FIGS. 1 and 2, the front and back waist portions, 26 and 32 respectively, see FIG. 1, are secured together to form a pair of side seams or seals 33 and 35, see FIG. 2. Each of the side seams 33 and 35 is depicted as a T-seal that extends inward toward the body of the user. Alternatively, each of the side seams 33 and 35 can be a T-seal that extends outward away from the body or can be a lap seal. The side seams 33 and 35 can be formed by using an ultrasonic bond, by using an adhesive, by using a pressure bond, by using a thermal bond, by using a combination of heat and pressure or by using another means known to those skilled in the art. The tubular configuration 38 has a waist opening 40 and a pair of leg opening 42 and 44. The disposable absorbent underpants 10 is designed to fit snugly around the torso of a user and is designed to contain body fluid, especially urine, discharged by the wearer.

Figure 3:
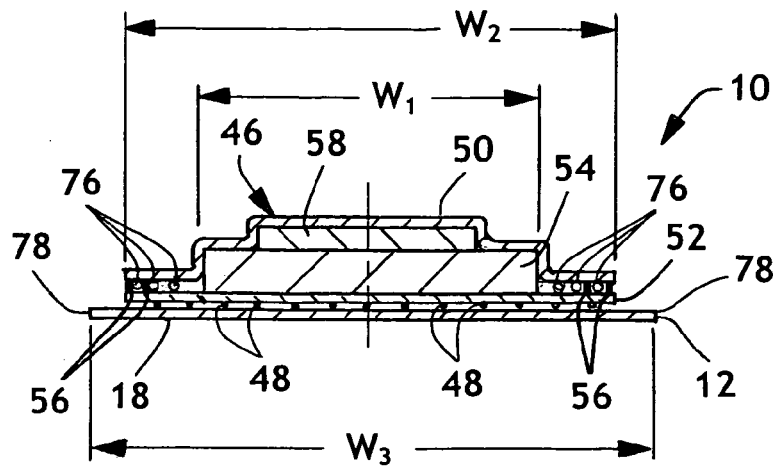
FIG. 3 is a cross-sectional view taken along line 3—3 of FIG. 1 showing the absorbent pad secured to the crotch portion of the outer cover.

Referring now to FIG. 3, an absorbent pad 46 is shown being secured directly to the liquid-impermeable outer cover 12. The absorbent pad 46 is positioned over the crotch portion 18 of the outer cover 12 by an adhesive 48. The adhesive 48 can be either a hot melt adhesive or a cold melt adhesive. The absorbent pad 46 has an hourglass configuration or profile and is sized to cover or overlap at least about 80% of the crotch portion 18. Desirably, the absorbent pad 46 is sized and configured to cover or overlap at least about 90% of the crotch portion 18. More desirably, the absorbent pad 46 is sized and configured to cover or overlap at least about 95% of the crotch portion 18. The absorbent pad 46 includes a liquid permeable cover 50, a liquid-impermeable baffle 52 and an absorbent layer 54 positioned therebetween. The liquid permeable cover 50 and the liquid-impermeable baffle 52 are joined or secured together about their peripheries by a construction adhesive 56. The construction adhesive 56 can be either a hot melt adhesive or a cold melt adhesive.

Referring to FIGS. 1 and 3, the absorbent layer 54 has a length $L_1$, see FIG. 1, and a width $W_1$, see FIG. 3, which are less than the length $L_2$ and the width $W_2$ of the absorbent pad 46. This means that the liquid permeable cover 50 and the liquid-impermeable baffle 52 are larger in size than the absorbent layer 54 and both extend beyond the outer periphery of the absorbent layer 54. This is important because by forming the absorbent layer 54 such that it has a smaller overall size than the absorbent pad 46, any body fluid received by the absorbent layer 54 will not be able to flow or wick outward to the outer edges of the absorbent pad 46. This feature will minimize and hopefully prevent fluid leakage from occurring. The absorbent layer 54 should have a width $W_1$ that is at least about 0.125 inches (about 0.32 mm) less than the width $W_2$ of the absorbent pad 46.

Desirably, the absorbent layer 54 will have a width $W_1$ that is from between about 0.25 inches (about 0.64 mm) to about 1 inch (about 25.4 mm) less than the width $W_2$ of the absorbent pad 46. More desirably, the absorbent layer 54 will have a width $W_1$ that is from between about 0.375 inches (about 9.5 mm) to about 0.75 inches (about 19 mm) less than the width $W_2$ of the absorbent pad 46.

Referring again to FIG. 3, one will notice that the crotch portion 18 of the outer cover 12 has a minimum width $W_3$. The width $W_2$ of the absorbent pad 46 is less than the minimum width $W_3$ Of the crotch portion 18. The absorbent pad 46 should have a width $W_2$ that is at least about 0.125 inches (about 3.2 mm) less than the width $W_3$ of the crotch portion 18. Desirably, the width $W_2$ of the absorbent pad 46 is from between about 0.25 inches (about 6.4 mm) to about 1 inch (about 25.4 mm) less than the width $W_3$ of the crotch portion 18. More desirably, the absorbent pad 46 will have a width $W_2$ that is from between about 0.375 inches (about 9.5 mm) to about 2 inches (about 51 mm) less than the width $W_3$ of the crotch portion 18. The reason for this size difference is that the disposable absorbent underpants 10 is primarily designed to absorb urine and it is desirable to confine the urine to the absorbent layer 54.

The absorbent layer 54 has a width $W_1$ that is less than the width $W_2$ of the absorbent pad 46 and, in turn, the absorbent pad 46 has a width $W_2$ that is less than the width $W_3$ of the crotch portion 18. This size difference assures that if any urine wicks to the longitudinal side edges of the absorbent layer 54, that it will still be spaced apart from the longitudinal side edges of the absorbent pad 46. In turn, the urine will be further spaced away from the arcuate side edges 76 of the crotch portion 18 and therefore will not leak onto the wearer's clothing or skin.

The liquid permeable cover 50 can be formed from a liquid permeable material so as to allow body fluid which strikes the absorbent pad 46 to pass down into the absorbent layer 54. The cover 50 can be formed from many different liquid permeable materials. Examples of some liquid permeable materials that work well include: a non-woven web, a spunbond, a meltblown or a bonded-carded web. A bonded-carded web can be composed of synthetic polymer filaments or fibers. Examples of synthetic materials include polypropylene, polyethylene, polyesters and the like. The liquid permeable cover 50 can also be formed from a perforated thermoplastic film. The liquid permeable cover 50 can further be formed from rayon or cotton or from other materials known to those skilled in the art. The liquid permeable cover 50 can also be treated with a surfactant to aid in the transfer of the body fluid into the absorbent layer 54, if desired.

The liquid-impermeable baffle 52 can be formed from a liquid-impermeable material so as to prevent body fluid that contacts it from passing therethrough. The liquid-impermeable baffle 52 can be formed from a thin sheet of thermoplastic material such as polyethylene, polypropylene, polyvinyl chloride and the like. Alternatively, the liquid-impermeable baffle 52 can be formed from a non-woven, fibrous web that has been constructed to have low liquid permeability. The liquid-impermeable baffle 52 can also be constructed from a foam material. In some instances, it may be advantageous to form the liquid-impermeable baffle 52 from a material that will allow vapors to pass through but which will prevent body fluid from passing through. Any material known to those skilled in the art which will prevent a liquid or body fluid from passing therethrough can be used for the liquid-impermeable baffle 52.

The absorbent layer 54 that is retained between the liquid permeable cover 50 and the liquid-impermeable baffle 52 should be primarily designed to absorb urine. However, it could be constructed to absorb other body fluids, such as menses, blood, perspiration, as well as other body excrements. The absorbent layer 54 can be formed from various natural and/or synthetic materials, such as cellulose fibers, wood pulp fibers, regenerated cellulose or cotton fibers, meltblown fibers, a blend of pulp and other fibers, or a combination of various fibers. A suitable material is "coform" which is a mixture of cellulose fibers and synthetic polymer fibers. Coform is manufactured by Kimberly-Clark Corporation, having an office at 401 North Lake Street, Neenah, Wis. 54956.

The absorbent layer 54 can also include superabsorbent materials, commonly referred to as "superabsorbents", to increase its absorbency and ability to retain body fluids under pressure loads. The superabsorbents can be present in particle form, as flakes or have some other structural shape. The superabsorbents can be secured to the absorbent fibers by an adhesive or they can be loosely positioned between the absorbent fibers. Suitable superabsorbents are commercially available from the Dow Chemical Company, Hoechst Celanese Corporation and Allied Colloids, Inc.

The absorbent layer 54 may be wrapped in tissue or some similar kind of acquisition and/or distribution layer to assist in maintaining the integrity of the absorbent fibers and the superabsorbents.

It should be noted that the absorbent pad 46 should be designed to absorb at least about 100 grams of body fluid, such as urine. Desirably, the absorbent pad 46 should be designed to absorb from between about 100 grams to about 1500 grams of body fluid. More desirably, the absorbent pad 46 should be designed to absorb about 300 grams of body fluid. Still more desirably, the absorbent pad 46 should be designed to absorb about 500 grams of body fluid. Even more desirably, the absorbent pad 46 should be designed to absorb about 1,000 grams of body fluid. Most desirably, the absorbent pad 46 should be designed to absorb about 1,500 grams of body fluid.

In order to measure the absorbency of the absorbent pad 46, one should use a "Saturated Retention Capacity Test." The "Saturated Retention Capacity" of the absorbent pad 46 can be measured using the following procedure. First, the absorbent pad 46 is measured to make sure it has a moisture content of less than about 7 weight percent. The moisture content value can be obtained by following the ASTM D-2495 (7.01) Standard Test Method for Moisture Content in Cotton by Oven-Drying. The absorbent pad 46 is then weighed to obtain its "dry weight." The absorbent pad 46 is then submerged in an excess quantity of synthetic urine at room temperature (about 23 degrees Celsius). The composition of the synthetic urine comprises 0.31 grams of monobasic calcium phosphate monohydrate (CaH4(PO4) 2H2O), 0.68 grams of monobasic potassium phosphate (KH2PO4), 0.48 grams of magnesium sulphate heptahydrate (MgSO4 7H2O), 1.33 grams of potassium sulphate (K2SO4), 1.24 grams of tribasic sodium phosphate dodecahydrate (Na3PO4 12H2O), 4.4 grams of sodium chloride (NaCl), 3.16 grams of potassium chloride (KCl), 8.56 grams of urea (CO(NH2)2), 0.1 grams of Pluronic 10R8 surfactant (a non-ionic surfactant commercially available from BASF-Wyandotte Corporation), 1 gram of methyl paraben and 1 gram of Germall 115 preservative (commercially available from Santell Chemical Company, Chicago, Ill.) per liter using distilled water as the solvent. The above-identified components are added to 900 milliliters of distilled water in the order given and each dissolved before the next component is added. The solution is finally diluted to one liter.

The absorbent pad 46 is allowed to remain submerged in the synthetic urine for 20 minutes. After 20 minutes, the absorbent pad 46 is removed from the synthetic urine and placed on a TEFLON coated fiberglass screen. TEFLON is a registered trademark of E. I. DuPont de Nemours & Company, having an office at 1002 Market Street, Wilmington, Del. 19801. The screen has a plurality of openings of about 0.25 inches (about 6.4 mm) in width. Such a screen is commercially available from Taconic Plastics, Inc., having an office in Petersburg, N.Y. The screen is positioned on a vacuum box and the absorbent pad 46 is positioned in direct contact with the upper surface of the screen. The absorbent pad 46 and screen are covered with a flexible rubber dam material. A vacuum of 3.5 kilopascals (about 0.5 pounds per square inch) is drawn into the vacuum box for a period of 5 minutes. The flexible rubber dam material is removed and the absorbent pad 46 is withdrawn and weighed to obtain its "wet weight." The amount of fluid retained by the absorbent pad 46 is determined by subtracting its dry weight from its wet weight. The "Saturated Retention Capacity" of the absorbent pad 46 is equal to the fluid, measured in grams, which is retained by the absorbent pad 46.

Optionally positioned above the absorbent layer 54 can be a surge layer 58. The surge layer 58 is in direct contact with the liquid permeable cover 50. The purpose of the surge layer 58 is to quickly take up body fluid that contacts the cover 50 and direct this body fluid downward toward the absorbent layer 54. In addition, the surge layer 58 can direct the body fluid outward in the transverse and longitudinal directions so that it is capable of contacting a greater surface area of the absorbent layer 54. The ability of the surge layer 58 to quickly move the body fluid in the x, y and z directions diffuses surges of body fluid which insult the absorbent pad 46. The surge layer 58 is also commonly referred to as an acquisition/distribution layer. The surge layer 58 can be formed from a through-air bonded-carded web composed of a blend of 40% 6 denier polyester fibers, commercially available from Hoechst Celanese Corporation, and 60% 3 denier polypropylene/polyethylene sheath core bicomponent fibers, commercially available from Chisso Corporation. The surge layer 58 can have an overall basis weight ranging from about 50 grams per square meter (gsm) to about 120 gsm. In FIG. 1, the surge layer 58 is depicted as having a rectangular configuration but it could be formed into other shapes as well, including an hourglass shape, an oval shape, etc.

Figure 4:
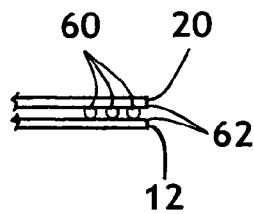
FIG. 4 is a cross-sectional view taken along line 4—4 of FIG. 1 showing one of the first pair of leg elastics sandwiched between the outer cover and the inner liner and positioned within 1 inch of the outer edge.

Referring to FIGS. 1 and 4, the disposable absorbent underpants 10 includes a first pair of leg elastics 60 secured between the outer cover 12 and the inner liner 20. The first pair of leg elastics 60 is present on the right and left sides of the front waist portion 26. Each of the first pair of leg elastics 60 is positioned adjacent to one of the pair of leg openings, 42 and 44 respectively. The first pair of leg elastics 60 is depicted as being three strands of an elastic material although a fewer or a greater number of strands can be utilized if desired. It has been found that three strands provide adequate elastic strength to form gathers about each of the leg openings 42 and 44. The first pair of leg elastics 60 can be secured at intermittent sites to the outer cover 12 and to the inner liner 20 by an adhesive, by ultrasonic bonding, by heat and/or pressure bonds or by some other means known to those skilled in the art. Materials suitable for forming the first pair of leg elastics 60 include polyurethane, rubber, and other elastomeric materials. The first pair of leg elastics 60 can be in the form of long or short elastic strands, elastic tapes, ribbons, yarns, etc. The first pair of leg elastics 60 can have a cross-sectional configuration that is flat, square, rectangular, circular, oval or some other shape. A good material from which the first pair of leg elastics 60 can be formed is LYCRA. LYCRA is a registered trademark of the E. I. DuPont de Nemours & Company that has an office at 1002 Market Street, Wilmington, Del. 19801.

Each of the first pair of leg elastics 60 is positioned adjacent to a first pair of edges 62. Each of the first pair of edges 62 is substantially linear in configuration and each extends inward toward the crotch portion 18 from one of the two distally spaced edges 28 and 30. At least about 50% of the length of each of the first pair of leg elastics 60 is linear in configuration. Desirably, from between about 70% to about 100% of each of the first pair of leg elastics 60 is linear in configuration. More desirably, from between about 75% to about 95% of each of the first pair of leg elastics 60 is linear in configuration.

Each of the first pair of edges 62 are aligned at an angle alpha ($\alpha$) to the longitudinal centerline X—X of the disposable absorbent underpants 10. The angle alpha ($\alpha$) can range from between about 62 degrees to about 99 degrees. Desirably, the angle alpha ($\alpha$) can range from between about 74 degrees to about 91 degrees, and most desirably, the angle alpha ($\alpha$) is at least about 85 degrees. The angling of the first pair of edges 62 relative to the longitudinal centerline X—X ensures a better contouring of the disposable absorbent underpants 10 to the body and provides a comfortable fit with reduced bunching.

Referring again to FIGS. 1 and 2, each of the first pair of leg elastics 60 is positioned within 1 inch (about 25.4 mm) of one of the leg openings, 42 and 44 respectively. Desirably, each of the first pair of leg elastics 60 is positioned within 0.5 inches (about 13 mm) of one of the leg openings, 42 and 44 respectively. More desirably, each of the first pair of leg elastics 60 is positioned within about 0.375 inches (about 9.5 mm) of one of the leg openings, 42 and 44 respectively. Even more desirably, each of the first pair of leg elastics 60 is positioned within about 0.25 inches (about 6.5 mm) of one of the leg openings, 42 and 44 respectively. By "positioned within" it is meant that each of the first pair of leg elastics 60 is located entirely within the specified dimension as measured from the adjacent edge 62.

Referring again to FIG. 1, each of the first pair of leg elastics 60 is located along and is preferably aligned parallel to at least a portion of the first pair of edges 62. Desirably, each of the first pair of leg elastics 60 is aligned parallel to at least about 80% of the first pair of edges 62. Each of the first pair of leg elastics 60 has a first end 64 located adjacent to or coterminous to one of the distal edges, 28 and 30 respectively. Desirably, each of the first ends 64 is spaced slightly inward from one of the two distal edges 28 and 30. The first pair of leg elastics 60 should extend toward the absorbent pad 46 but should stop short thereof. Each of the first pair of leg elastics 60 terminates at a second end 66. The first pair of leg elastics 60 should extend toward the absorbent pad 46 but should stop short thereof. Each of the second ends 66 is located away from the longitudinal edges of the absorbent pad 46. The exact distance that each of the second ends 66 is spaced away from the longitudinal edges of the absorbent pad 46 can vary from between about 3 millimeter to about 75 millimeters. Desirably, the distance from the longitudinal edges of the absorbent pad 46 to each of the second ends 66 is less than about 25 millimeters. This spacing is to assure that the first pair of leg elastics 60 can function properly without interfering with the absorbent pad

46. By the "first and second ends, 64 and 66 respectively," of the first pair of leg elastics 60, it is meant the ends of the gathered material where the effectiveness of the elastic ends. This can differ from the physical ends of the elastic material which is normally longer and represents the actual ends of the individual elastic filaments or strands.

The disposable absorbent underpants 10 also includes a second pair of leg elastics 68 secured between the outer cover 12 and the inner liner 20. The second pair of leg elastics 68 is present on the right and left sides of the back waist portion 32. Each of the second pair of leg elastics 68 is positioned adjacent to one of the pair of leg openings, 42 and 44 respectively. The second pair of leg elastics 68 is depicted as being three strands of an elastic material although a fewer or a greater number of strands can be utilized if desired. It has been found that three strands provide adequate elastic strength to form gathers about each of the leg openings 42 and 44, see FIG. 2. The second pair of leg elastics 68 can be secured at intermittent sites to the outer cover 12 and to the inner liner 20 by an adhesive, by ultrasonic bonding, by heat and/or pressure bonds or by some other means known to those skilled in the art. Materials suitable for forming the second pair of leg elastics 68 include those described above with reference to the first pair of leg elastics 60. Like the first pair of leg elastics 60, the second pair of leg elastics 68 can be in the form of long or short elastic strands, elastic tapes, ribbons, yarns, etc. The second pair of leg elastics 68 can have a cross-sectional configuration that is flat, square, rectangular, circular, oval or some other shape.

Each of the second pair of leg elastics 68 is positioned adjacent to a second pair of edges 70. Each of the second pair of edges 70 is substantially linear in configuration and extends inward toward the crotch portion 18 from the two distally spaced edges 34 and 36. At least about 50% of the length of each of the second pair of leg elastics 68 is linear in configuration. Desirably, from between about 70% to about 100% of each of the second pair of leg elastics 68 is linear in configuration. More desirably, from between about 75% to about 95% of each of the second pair of leg elastics 68 is linear in configuration.

Each of the second pair of edges 70 is aligned at an angle beta (β) to the longitudinal centerline X—X of the disposable absorbent underpants 10. The angle beta (β) can range from between about 45 degrees to about 89 degrees. Desirably, the angle beta (β) can range from between about 55 degrees to about 87 degrees, and most desirably, the angle beta (β) is from between about 61 degrees to about 76 degrees. The angling of the second pair of edges 70 relative to the longitudinal centerline X—X ensures a better contouring of the disposable absorbent underpants 10 to the body and provides a comfortable fit with reduced bunching.

Referring again to FIGS. 1 and 2, each of the second pair of leg elastics 68 is positioned within 1 inch (about 25.4 mm) of one of the leg openings, 42 and 44 respectively. Desirably, each of the second pair of leg elastics 68 is positioned within 0.5 inches (about 13 mm) of one of the leg openings, 42 and 44 respectively. More desirably, each of the second pair of leg elastics 68 is positioned within about 0.375 inches (about 9.5 mm) of one of the leg openings, 42 and 44 respectively. Even more desirably, each of the second pair of leg elastics 68 is positioned within about 0.25 inches (about 6.5 mm) of one of the leg openings, 42 and 44 respectively. By "positioned within" it is meant that each of the second pair of leg elastics 68 is located entirely within the specified dimension as measured from the adjacent edge 70.

Referring again to FIG. 1, each of the second pair of leg elastics 68 is located along and is preferably aligned parallel to at least a portion of the second pair of edges 70. Desirably, each of the second pair of leg elastics 68 is aligned parallel to at least about 80% of the second pair of edges 70. Each of the second pair of leg elastics 68 has a first end 72 located adjacent to or coterminous to one of the distal edges, 34 and 36 respectively, of the back portions 16 and 24. Desirably, each of the first ends 72 is spaced slightly inward from one of the two edges 34 and 36. The second pair of leg elastics 68 should extend toward the absorbent pad 46 but should stop short thereof. Each of the second pair of leg elastics 68 terminates at a second end 74. Each of the second ends 74 is located away from the outer periphery of the absorbent pad 46. The exact distance can vary from between about 3 millimeter to about 50 millimeters. Desirably, the distance from the outer periphery of the absorbent pad 46 to one of the second ends 74 is less than about 25 millimeters. As stated above with reference to the first pair of leg elastics 60, the first and second ends, 72 and 74 respectively, of the second pair of leg elastics 68 refer to the gathered end of the elastic material and not to the actual length of the individual elastic filaments or strands.

The disposable absorbent underpants 10 further includes a third pair of leg elastics 76 secured between the liquid permeable cover 50 and the liquid-impermeable baffle 52 that form the absorbent pad 46. The third pair of leg elastics 76 has an arcuate profile. The third pair of leg elastics 76 is present on the right and left sides of the crotch portion 18. Each of the third pair of leg elastics 76 is positioned adjacent to one of the pair of leg openings, 42 and 44 respectively. The third pair of leg elastics 76 is depicted as being three strands of an elastic material although a fewer or a greater number of strands can be utilized if desired. It has been found that three strands provide adequate elastic strength to form gathers about each of the leg openings 42 and 44. The third pair of leg elastics 76 can be secured at intermittent sites to the liquid permeable cover 50 and to the liquid-impermeable baffle 52 by an adhesive, by ultrasonic bonding, by heat and/or pressure bonds or by some other means known to those skilled in the art. Materials suitable for forming the third pair of leg elastics 76 include those described above with reference to the first and second pairs of leg elastics, 60 and 68 respectively. Like the first and second pairs of leg elastics, 60 and 68 respectively, the third pair of leg elastics 76 can be in the form of long or short elastic strands, elastic tapes, ribbons, yarns, etc. The third pair of leg elastics 76 can have a cross-sectional configuration that is flat, square, rectangular, circular, oval or some other shape.

Referring to FIGS. 1 and 3, each of the third pair of leg elastics 76 is positioned adjacent to a third pair of side edges 78. The side edges 78 are arcuate, or curved in configuration and each is located adjacent to the outside periphery of the crotch portion 18. Each of the third pair of leg elastics 76 is aligned parallel to at least a portion of one of the third pair of side edges 78. Desirably, each of the third pair of leg elastics 76 is aligned parallel to at least about 90% of one of the third pair of edges 78. More desirably, each of the third pair of leg elastics 76 is aligned parallel to about 100% of one of the third pair of edges 78. Each of the third pair of leg elastics 76 is positioned within 1 inch (about 25.4 mm) of one of the leg openings, 42 and 44 respectively. Desirably, each of the third pair of leg elastics 76 is positioned within 0.5 inches (about 13 mm) from one of the leg openings, 42 and 44 respectively, see FIG. 3. More desirably, each of the third pair of leg elastics 76 is positioned within about 0.375 inches (about 9.5 mm) from one of the leg openings, 42 and 44 respectively. Even more desirably, each of the third pair of leg elastics 76 is positioned within about 0.25 inches (about 6.5 mm) from one of the leg openings, 42 and 44 respectively. By "positioned within" it is meant that each of the third pair of leg elastics 76 is located entirely within the specified dimension as measured from the adjacent third pair of side edges 78.

Referring again to FIG. 1, each of the third pair of leg elastics 76 is located along one of the side edges 78 and is aligned parallel thereto. Each of the third pair of leg elastics 76 is positioned intermediate one of the first and second pairs of leg elastics, 60 and 68 respectively. Each of the third pair of leg elastics 76 has a first end 80 and a second end 82. As stated above with reference to the first and second pairs of leg elastics, 60 and 68 respectively, the first and second ends, 80 and 82 respectively, of the third pair of leg elastics 76 refer to the gathered end of the elastic material and not to the actual length of the individual elastic filaments or strands.

The first ends 80 of the third pair of leg elastics 76 are separated from the second ends 66 of the first pair of leg elastics 60 by a first pair of gaps 84. The dimension of each of the first pair of gaps 84 is denoted as "$D_1$." The dimension $D_1$ can be at least about 0.125 inches (about 3.2 mm) in length. Desirably, the dimension $D_1$ is from between about 0.25 inches (about 6.4 mm) to about 9 inches (about 229 mm). More desirably, the dimension $D_1$ is from between about 0.375 inches (about 9.5 mm) to about 5 inches (about 127 mm). Most desirably, the dimension $D_1$ is from between about 0.5 inches (about 13 mm) to about 2 inches (about 51 mm). The dimension $D_1$ is measured when the disposable absorbent underpants 10 is in a flat, extended orientation similar to that depicted in FIG. 1. To measure the distance of the gaps $D_1$, one should mark the gathered ends 66 and 80 of the first and third pairs of leg elastics 60 and 76 when the disposable absorbent underpants 10 is in a relaxed state. In this state, the disposable absorbent underpants 10 is opened to the configuration shown in FIG. 1. The disposable absorbent underpants 10 is then stretched or extended 100% along the longitudinal centerline X—X while still in a flat configuration. The dimension of each of the first pair of gaps 84 will increase. In this configuration, the first and third pairs of leg elastics, 60 and 76 respectively, will be stretched from their relaxed state and the actual distance between the marks will represent the dimension of the gap $D_1$.

Likewise, the second ends 82 of the third pair of leg elastics 76 are separated from the second ends 74 of the second pair of leg elastics 68 by a second pair of gaps 86. The dimension of each of the second pair of gaps 86 is denoted as "$D_2$." The dimension $D_2$ can be at least about 0.125 inches (about 3.2 mm) in length. Desirably, the dimension $D_2$ is from between about 0.25 inches (about 6.4 mm) to about 9 inches (about 229 mm). More desirably, the dimension $D_2$ is from between about 0.375 inches (about 9.5 mm) to about 5 inches (about 127 mm). Most desirably, the dimension $D_2$ is from between about 0.5 inches (about 13 mm) to about 2 inches (about 51 mm). The dimension $D_2$ is measured when the disposable absorbent underpants 10 is in a flat, extended orientation similar to that depicted in FIG. 1. To measure the distance of the gap $D_2$, one should mark the gathered ends 74 and 82 of the second and third pairs of leg elastics 68 and 76 in a relaxed state. The disposable absorbent underpants 10 is then stretched or extended 100% along the longitudinal centerline X—X while still in a flat configuration. The dimension of each of the second pair of gaps 86 will increase. In this configuration, the second and third pairs of leg elastics, 68 and 76 respectively, will be stretched from their relaxed state and the actual distance between the marks will represent the dimension of the gap $D_2$.

It should be noted that two pairs of gaps 84 and 86 have been described. However, if one desired to use only one pair of the two pairs of gaps, 84 and 86, this can be done. One could also use additional gaps, if desired, without destroying the function of this invention. Desirably, the two pairs of gaps 84 and 86 will be sufficient.

The first and second pairs of gaps, 84 and 86 respectively, ensure that the first, second and third pairs of leg elastics, 60, 68 and 76 respectively, will cooperate together to form gathers 88 and 90 around the first and second leg openings, 42 and 44 respectively. The gathers 88 and 90, best depicted in FIG. 2, form a snug fit around the entire circumference of each of the leg openings 42 and 44. The two pairs of gaps 84 and 86 will prevent the adjacent leg elastics 60, 68 and 76 from overlapping one another and forming bumps and/or humps around the leg openings 42 and 44. By eliminating such bumps and humps, one can prevent the leakage of body fluid through the leg openings 42 and 44. It is very important that fluid leakage from around the leg openings 42 and 44 be minimized and hopefully eliminated because if such leakage occurs, the usefulness of the disposable absorbent underpants 10 is compromised.

Even though the two pairs of gaps 84 and 86 are present in the stretched out, flat orientation shown in FIG. 1, the contraction force of the first, second and third pairs of leg elastics 60, 68 and 76 will cause the gathers 88 and 90 to form. The force of the leg elastics 60, 68 and 76 adjacent to the gaps 84 and 86 will cause the material forming the outer cover 12 and the inner liner 20 to fit snug against the thighs of the wearer during use. No fluid channels will occur at the locations of the first and second pairs of gaps 84 and 86. This will assure that no body fluid will be able to leak out through these locations ($D_1$ and $D_2$) during normal use.

Referring again to FIGS. 1 and 2, the disposable absorbent underpants 10 further has waist elastic 92 attached to the front waist portion 26 and waist elastic 94 attached to the back waist portion 32. The waist elastics 92 and 94 can include threads, strands, ribbons, bands, film, elastic nonwovens or composites. The threads, strands, ribbons, etc. may be a multitude of singular members or they may be applied as a composite. The number of elastic members can range from 1 to over a 100. Desirably, the number of elastic members 92 and 94 will range from between about 10 to about 40, and most desirably, from about 15 to about 35. There can be an equal number or a different number of waist elastics 92 in the front waist portion 26 versus the number of waist elastics 94 in the back waist portion 32. The waist elastics 92 and 94 can be individual threads that are spaced apart from one another from between about 0.063 inches (about 1.6 mm) to about 2.0 inches (about 51 mm) Desirably, the waist elastics 92 and 94 can be individual threads that are spaced apart from one another by about 0.25 inches (about 6 mm). While the appearance of the disposable absorbent underpants 10 may be enhanced by the close even spacing of the waist elastics 92 and 94, the exact distance between adjacent waist elastics 92 or 94 can vary.

The waist elastics 92 and 94 may be made from any suitable elastomeric material. One suitable material is LYCRA. LYCRA is a registered trademark of the E. I. DuPont de Nemours & Company, having an office at 1002 Market Street, Wilmington, Del. 19801. Suitable waist elastics 92 and 94 include threads having a decitex (grams/10,000 meters) of from between about 100 to about 1,200. Desirably, the waist elastics 92 and 94 are threads having a decitex of from between about 470 to about 940. More desirably, the waist elastics 92 and 94 are threads having a decitex of from between about 620 to about 740. The waist elastics 92 and 94 can be secured to the outer cover 12 and to the inner liner 20 by a hot or cold melt adhesive applied in a variety of spray patterns. One spray pattern that has been used with good success is a swirl pattern. An adhesive that works well is a hot melt adhesive sold as Findley H2096 by ATO Findley Adhesives, having an office in Milwaukee, Wis.

Figure 6:
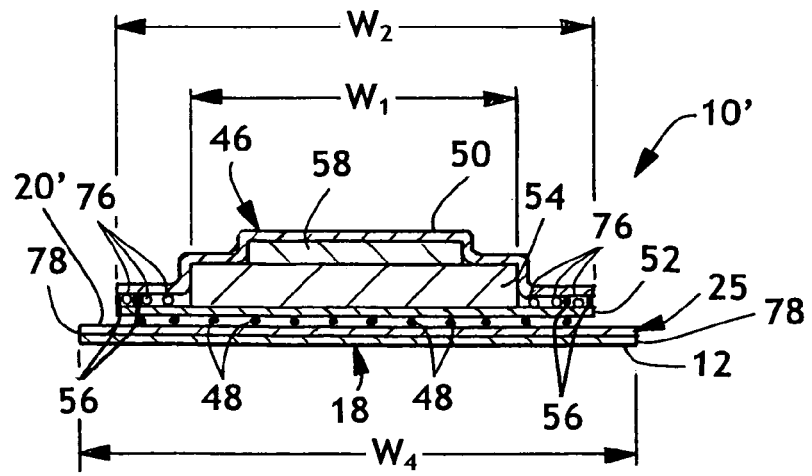
FIG. 6 is a cross-sectional view taken along line 6—6 of FIG. 5 showing the absorbent pad secured to the crotch portion of the inner liner.
Figure 5:
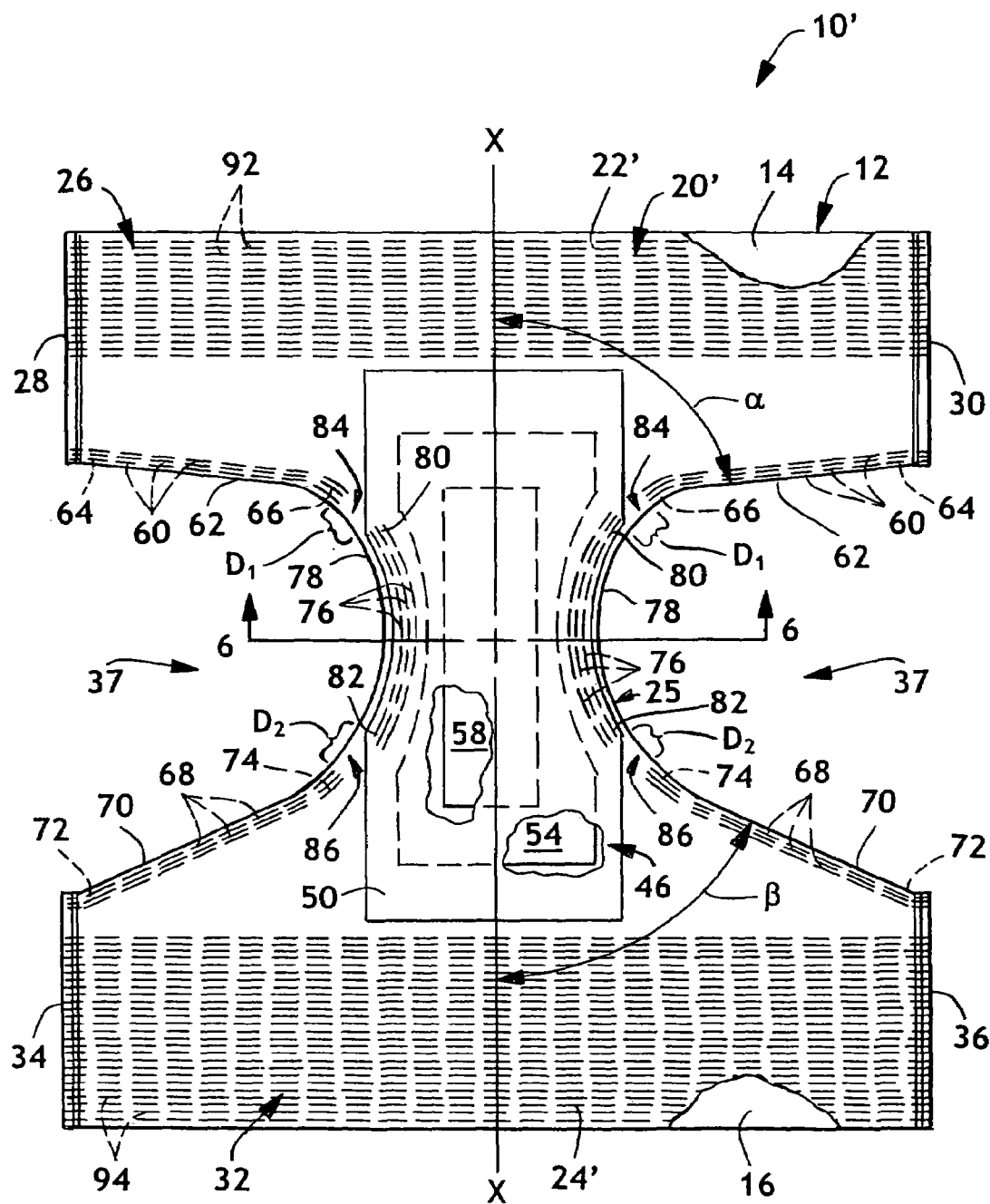
FIG. 5 is a top view of an alternative disposable absorbent underpants before the front and back portions are joined together and showing cut-away sections depicting an outer cover and an inner liner with coterminous edges and various layers of the absorbent pad, along with three discrete sections of leg elastics surrounding each of the pair of leg cutouts wherein each of the three elastic sections are separated from one another by a gap.

Referring now to FIGS. 5 and 6, an alternative embodiment of a disposable absorbent underpants 10' is depicted. Most of the numbers used in FIGS. 1–4 will be reused to connote identical structure in FIGS. 5 and 6. In this embodiment, the disposable absorbent underpants 10' includes an inner liner 20' having a front portion 22' and a back portion 24' joined together by a crotch portion 25. The inner liner 20' should be soft and flexible. The inner liner 20' can be liquid permeable or liquid-impermeable. Desirably, the inner liner 20' is liquid permeable. In the disposable absorbent underpants 10', the inner liner 20' can be a single piece of material or it could be assembled from two or more pieces of material. Desirably, the inner liner 20' will be a single piece of material.

The crotch portion 25 can overlay the crotch portion 18 of the outer cover 12. The crotch portion 25 can be bonded to the crotch portion 18 of the outer cover 12 or it can merely be in contact therewith. Alternatively, the crotch portion 18 of the outer cover 12 can be eliminated when the crotch portion 25 of the inner liner 20' is present. Since the inner liner 20' includes the crotch portion 25, the absorbent pad 46 will be secured thereto. This is different from the disposable absorbent underpants 10 shown in FIG. 1, wherein the inner liner 20 did not include a crotch portion. In FIG. 1, the absorbent pad 46 was secured directly to the crotch portion 18 of the outer cover 12. When the inner liner 20' does include a crotch portion 25, it is advantageous to secure the absorbent pad 46 directly to it.

Referring to FIG. 6, one will notice that the absorbent layer 54 has a width $W_1$ and the absorbent pad 46 has a width $W_2$. In addition, the crotch portion 18 of the outer cover 12 has a minimum width $W_3$ and the crotch portion 25 of the inner liner 20' has a minimum width $W_4$. The width $W_3$ is approximately equal to the width $W_4$. Desirably, the width $W_3$ is equal to the width $W_4$. The width $W_2$ of the absorbent pad 46 is less than the minimum width $W_4$ of the crotch portion 25. In turn, the width $W_2$ of the absorbent pad 46 is greater than the width $W_1$ of the absorbent layer 54. The absorbent pad 46 should have a width $W_2$ that is at least about 0.125 inches (about 3.2 mm) less than the width $W_4$ of the crotch portion 25. Desirably, the width $W_2$ of the absorbent pad 46 is from between about 0.25 inches (about 6.4 mm) to about 1 inch (about 25.4 mm) less than the width $W_4$ of the crotch portion 25. More desirably, the absorbent pad 46 will have a width $W_2$ that is from between about 0.375 inches (about 9.5 mm) to about 2 inches (about 51 mm) less than the width $W_4$ of the crotch portion 25. The reason for this size difference is that the disposable absorbent underpants 10 is primarily designed to absorb urine and it is desirable to confine the urine to the absorbent layer 54.

In FIGS. 5 and 6, the hourglass shaped absorbent pad 46 is shown being secured directly to the liquid permeable inner liner 20'. The absorbent pad 46 is positioned over the crotch portion 25 of the inner liner 20' by an adhesive 48. The adhesive 48 can be either a hot melt adhesive or a cold melt adhesive. The absorbent pad 46 has an hourglass configuration or profile and is sized to cover or overlap at least about 80% of the crotch portion 25. Desirably, the absorbent pad 46 is sized and configured to cover or overlap at least about 90% of the crotch portion 25. More desirably, the absorbent pad 46 is sized and configured to cover or overlap at least about 95% of the crotch portion 25.

In FIGS. 5 and 6, just as in FIG. 1, the front and back portions, 22' and 24' respectively, of the inner liner 20' are attached to the front and back portions, 14 and 16 respectively, of the outer cover 12. The front and back waist portions, 26 and 32 respectively, are in turn seamed or sealed together to form a tubular configuration similar to that depicted in FIG. 2.

While the invention has been described in conjunction with two specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A disposable absorbent underpants for containing body fluid comprising:

a) an outer cover having a front portion and a back portion joined together by a crotch portion, said crotch portion having an hourglass configuration with a minimum width $W_3$;

b) an inner liner having a front portion and a back portion, said front and back portions of said inner liner being attached to said front and back portions, respectively, of said outer cover, and said inner liner and said outer cover being joined together to form a waist opening and a pair of leg openings;

c) an absorbent pad including a liquid permeable cover, a liquid-impermeable baffle and an absorbent layer positioned therebetween, said baffle being secured to said crotch portion of said outer cover, said absorbent pad having a width $W_2$ which is less than said width $W_3$, and said absorbent pad overlapping at least about 80% of said crotch portion;

d) a first pair of leg elastics secured between said outer cover and said inner liner at said front portion, at least a portion of the length of each of said first pair of leg elastics being aligned parallel to an edge of one of said leg openings, and each of said first pair of leg elastics being positioned within 1 inch of one of said pair of leg openings;

e) a second pair of leg elastics secured between said outer cover and said inner liner at said back portion, at least a portion of the length of each of said second pair of leg elastics being aligned parallel to an edge of one of said leg openings, and each of said second pair of leg elastics being positioned within 1 inch of one of said pair of leg openings;

f) a third pair of leg elastics secured between said liquid permeable cover and said liquid-impermeable baffle, said third pair of leg elastics having an arcuate profile, each of said third pair of leg elastics being positioned within 1 inch of one of said leg openings intermediate one of said first and second pairs of leg elastics, each of said third pair of leg elastics being separated from one of each of said first pair of leg elastics by a first gap of at least about 0.125 inches and each of said third pair of leg elastics being separated from one of each of said second pair of leg elastics by a second gap of at least about 0.125 inches, said first, second and third pairs of leg elastics allowing gathers to form about each of said leg openings to prevent leakage of body fluid from said underpants; and g) waist elastic attached between said outer cover and said inner liner at said front and back portions, said waist elastics allowing gathers to form about said waist opening to prevent leakage of body fluid from said underpants.

2. The disposable absorbent underpants of claim 1 wherein said absorbent pad overlaps at least about 90% of said crotch portion.

3. The disposable absorbent underpants of claim 2 wherein said absorbent pad overlaps at least about 95% of said crotch portion.

4. The disposable absorbent underpants of claim 1 wherein each of said first and second gaps has a dimension of at least about 0.25 inches.

5. The disposable absorbent underpants of claim 4 wherein each of said first and second gaps has a dimension of from between about 0.25 inches to about 9 inches.

6. The disposable absorbent underpants of claim 1 wherein said crotch portion has a third pair of edges and each of said third pair of leg elastics is aligned parallel to at least about 90% of one of said third pair of edges.

7. The disposable absorbent underpants of claim 6 wherein said crotch portion has a third pair of edges and each of said third pair of leg elastics is aligned parallel to about 100% of one of said third pair of edges.

8. The disposable absorbent underpants of claim 1 wherein said absorbent pad has a capacity for absorbing about 500 grams of body fluid.

9. The disposable absorbent underpants of claim 8 wherein said absorbent pad has a capacity for absorbing about 1,000 grams of body fluid.

10. A disposable absorbent underpants for containing body fluid comprising:
   a) an outer cover having a front portion and a back portion joined together by a crotch portion, said crotch portion having an hourglass configuration with a minimum width $W_3$;
   b) an inner liner having a front portion and a back portion, said front and back portions of said inner liner being attached to said front and back portions, respectively, of said outer cover, and said inner liner and said outer cover being joined together to form a waist opening and a pair of leg openings;
   c) an absorbent pad including a liquid permeable cover, a liquid-impermeable baffle and an absorbent layer positioned therebetween, said baffle being secured to said crotch portion of said outer cover, said absorbent pad having a capacity for absorbing at least about 100 grams of body fluid, said absorbent pad having a width $W_2$ which is less than said width $W_3$, and said absorbent pad overlapping at least about 80% of said crotch portion;
   d) a first pair of leg elastics secured between said outer cover and said inner liner at said front portion, at least a portion of the length of each of said first pair of leg elastics being aligned parallel to an edge of one of said leg openings, and each of said first pair of leg elastics being positioned within 1 inch of one of said pair of leg openings;
   e) a second pair of leg elastics secured between said outer cover and said inner liner at said back portion, at least a portion of the length of each of said second pair of leg elastics being aligned parallel to an edge of one of said leg openings, and each of said second pair of leg elastics being positioned within 1 inch of one of said pair of leg openings;
   f) a third pair of leg elastics secured between said liquid permeable cover and said liquid-impermeable baffle, said third pair of leg elastics having an arcuate profile, each of said third pair of leg elastics being positioned within 1 inch of one of said leg openings intermediate one of said first and second pairs of leg elastics, each of said third pair of leg elastics being separated from one of each of said first pair of leg elastics by a first gap of at least about 0.125 inches and each of said third pair of leg elastics being separated from one of each of said second pair of leg elastics by a second gap of at least about 0.125 inches, said first, second and third pairs of leg elastics allowing gathers to form about each of said leg openings to prevent leakage of body fluid from said underpants; and
   g) waist elastic attached between said outer cover and said inner liner at said front and back portions, said waist elastics allowing gathers to form about said waist opening to prevent leakage of body fluid from said underpants.

11. The disposable absorbent underpants of claim 10 wherein said absorbent pad overlaps at least about 90% of said crotch portion.

12. The disposable absorbent underpants of claim 11 wherein said absorbent pad overlaps at least about 95% of said crotch portion.

13. The disposable absorbent underpants of claim 10 wherein from about 70% to about 100% of each of said first pair of leg elastics is linear in configuration.

14. The disposable absorbent underpants of claim 10 wherein from about 70% to about 100% of each of said second pair of leg elastics is linear in configuration.

15. The disposable absorbent underpants of claim 10 wherein said crotch portion has a third pair of edges and each of the third pair of leg elastics is aligned parallel to at least about 90% of one of said third pair of edges.

16. A disposable absorbent underpants for containing body fluid comprising:
   a) an outer cover having a front portion and a back portion joined together by a crotch portion, said crotch portion having an hourglass configuration with a minimum width $W_3$;
   b) an inner liner having a front portion and a back portion joined together by a crotch portion, said crotch portion having an hourglass configuration with a minimum width $W_4$ wherein $W_4$ is equal to $W_3$, and said inner liner and said outer cover being joined together to form a waist opening and a pair of leg openings;
   c) an absorbent pad including a liquid permeable cover, a liquid-impermeable baffle and an absorbent layer positioned therebetween, said baffle being secured to said crotch portion of said inner liner, said absorbent pad having a capacity for absorbing at least about 500 grams of body fluid, said absorbent pad having a width $W_2$ which is less than said width $W_3$, and said absorbent pad overlapping at least about 80% of said crotch portion;
   d) a first pair of leg elastics secured between said outer cover and said inner liner at said front portion, at least a portion of the length of each of said first pair of leg elastics being aligned parallel to an edge of one of said leg openings, and each of said first pair of leg elastics being positioned within 1 inch of one of said pair of leg openings;

e) a second pair of leg elastics secured between said outer cover and said inner liner at said back portion, at least a portion of the length of each of said second pair of leg elastics being aligned parallel to an edge of one of said leg openings, and each of said second pair of leg elastics being positioned within 1 inch of one of said pair of leg openings;

f) a third pair of leg elastics secured between said liquid permeable cover and said liquid-impermeable baffle, said third pair of leg elastics having an arcuate profile, each of said third pair of leg elastics being positioned within 1 inch of one of said leg openings intermediate one of said first and second pairs of leg elastics, each of said third pair of leg elastics being separated from one of each of said first pair of leg elastics by a first gap of at least about 0.125 inches and each of said third pair of leg elastics being separated from one of each of said second pair of leg elastics by a second gap of at least about 0.125 inches, said first, second and third pairs of leg elastics allowing gathers to form about each of said leg openings to prevent leakage of body fluid from said underpants; and g) waist elastic attached between said outer cover and said inner liner at said front and back portions, said waist elastics allowing gathers to form about said waist opening to prevent leakage of body fluid from said underpants.

17. The disposable absorbent underpants of claim 16 wherein said absorbent pad has a capacity for absorbing about 1,000 grams of body fluid.

18. The disposable absorbent underpants of claim 17 wherein said absorbent pad has a capacity for absorbing about 1,500 grams of body fluid.

19. The disposable absorbent underpants of claim 16 wherein said crotch portion has a third pair of edges forming an hourglass profile and each of the third pair of leg elastics is aligned parallel to about 100% of one of said third pair of edges.

20. The disposable absorbent underpants of claim 16 wherein from about 75% to about 95% of each of said first pair of leg elastics is linear in configuration.

* * * * *